United States Patent [19]
Tritsch et al.

[11] Patent Number: 6,030,645
[45] Date of Patent: Feb. 29, 2000

[54] FREE-FLOWING DRY PARTICLES

[75] Inventors: Jean-Claude Tritsch, Saint-Louis, France; Johann Ulm, Oberwil, Switzerland

[73] Assignee: Roche Vitamins Inc., Nutley, N.J.

[21] Appl. No.: 09/027,328

[22] Filed: Feb. 20, 1998

[30] Foreign Application Priority Data

Feb. 28, 1997 [CH] Switzerland ................. 482/97

[51] Int. Cl.⁷ ..................................... A61K 9/14
[52] U.S. Cl. ........................... 424/490; 424/494
[58] Field of Search ................ 426/464; 424/465, 424/489, 494, 488, 78.02, 78.03; 526/194

[56] References Cited

U.S. PATENT DOCUMENTS

| | | |
|---|---|---|
| 2,756,177 | 7/1956 | Cannalonga et al. . |
| 2,858,215 | 10/1958 | Espoy . |
| 3,247,064 | 4/1966 | Hideyuki et al. . |
| 3,445,563 | 5/1969 | Clegg et al. . |
| 4,519,961 | 5/1985 | Schumacher et al. . |
| 4,603,143 | 7/1986 | Schmidt . |
| 4,670,247 | 6/1987 | Scialpi . |
| 4,780,309 | 10/1988 | Geria et al. . |
| 4,906,478 | 3/1990 | Valentine et al. . |
| 5,556,617 | 9/1996 | Ribier et al. ............... 424/78.02 |
| 5,830,960 | 11/1998 | Sojka ............................ 526/194 |

FOREIGN PATENT DOCUMENTS 074 050  3/1983  European Pat. Off. .

*Primary Examiner*—Thurman K. Page
*Assistant Examiner*—W. Benston
*Attorney, Agent, or Firm*—Mark E. Waddell; Stephen M. Haracz; Bryan Cave LLP

[57] ABSTRACT

The invention is concerned with a flowable dry particle consisting of at least one oleophilic substance as the active ingredient present in a matrix of at least one carrier material and a coating. The coating consists of calcium silicate or of a mixture of calcium silicate with one or more mixture components, with the mixture components being microcrystalline cellulose, magnesium silicate, magnesium oxide, stearic acid, calcium stearate, magnesium stearate, silicon dioxide, kaolin and/or hydrogenated vegetable oil.

21 Claims, No Drawings

FREE-FLOWING DRY PARTICLES

BACKGROUND OF THE INVENTION

Flowable dry particles containing at least one oleophilic substance as the active ingredient present in a matrix of at least one carrier material and a coating are known. Their maximum content of oleophilic substance as the active ingredient has been 50 wt. %.

One process for the manufacture of such particles is described, for example, in German Patent 10 35 319 and in the corresponding U.S. Pat. No. 2,756,177, where a dispersion of an oily vitamin as the active ingredient is sprayed into a large excess of a starch powder having a water content below 8%, whereby the dry starch powder catches the spray particles and the spray particles remove an amount of water such that they solidify and are simultaneously coated with starch powder. A serious disadvantage of these particles is that about 15% of the amount of starch adheres to their surface and therefore the particles contain only a relatively low amount of active ingredient.

According to a similar process described in U.S. Pat. No. 3,445,563 the starch is replaced by a mixture of inorganic substances which absorb water and which do not absorb water in order to eliminate the danger of explosion which emanates from the finely divided starch. A 20-fold excess of the catch powder is necessary in order to obtain optimal results. As a water-absorbing component of the catch powder there is named, inter alia, calcium silicate, especially calcium aluminium silicate, as the oil-soluble active ingredient there is mentioned vitamin A and vitamin D. In the case of an active ingredient activity lying between 245 000 and 532 000 I.U./g the particles obtained contain up to 19% catch powder as the coating.

Further, a process has become known from European Patent Application 0074050 which is useful for the manufacture of dry, free-flowing powders of readily oxidizable substances, such as the vitamins or carotenoids, which are coated with a colloid. The process comprises dispersing these substances in an aqueous solution of a film-forming colloid, with the colloid being the homogeneous phase. With the addition of one or more substances from the group of mono-, di- or polysaccharides the dispersion is sprayed into a spray tower with the co-use of a spray aid agent and the sprayed particles are collected in a fluidized bed. Thereby, a hydrophobic silicic acid or a metal salt of a higher fatty acid or a mixture with silicic acid in a 0.02- to 0.15-fold amount by weight based on the dispersion is introduced as the spray aid agent above the fluidized bed with homogeneous distribution in the spray area at temperatures at which a solidification of the colloid of the sprayed particles does not yet occur. The particles loaded with aid agent, the colloid mass of which is essentially not gelled, is collected in a fluidized bed and the particles are dried in the fluidized bed in a manner known per se.

Although in this process only a thin, hydrophobic film of the spray aid agent is produced, the particles formed during the spraying are sufficiently stabilized to prevent an agglomeration of the particles when they come together in the non-solidified state, such that the direct drying subsequently is possible on a fluidized bed drier, the proposed process has the substantial disadvantage that hydrophobic silicic acid is used as the spray aid. The use of free silicic acid in the pharmaceutical or foodstuff industry, where further processing is carried out, is at least questionable, since it endangers health and is therefore not permitted for this purpose in many countries.

Therefore, the said process and the flowable dry particles of the aforementioned kind which are manufactured accordingly are not satisfactory, especially for use in the pharmaceutical or foodstuff industry.

SUMMARY OF THE INVENTION

The invention is concerned with flowable dry particles consisting of at least one oleophilic substance as the active ingredient present in a matrix of at least one carrier material and a coating.

DETAILED DESCRIPTION OF THE INVENTION

The object of the present invention is accordingly flowable dry particles having an oleophilic active ingredient content of above 50 wt. %, especially of above 70 wt. % up to 80%, i.e., particles having a high content of an oleophillic active ingredient, and a process for the manufacture of such particles. The invention is, furthermore, a solid unit dosage form prepared with these flowable dry particles in order to incorporate an amount of oleophilic active ingredient which is as high as possible in the unit dosage form.

The present invenion comprises a flowable dry particle having a size in the range from about 80 µm to about 1000 µm comprising:
    a core which contains an oleophilic active ingredient dispersed in a carrier material, and
    a coating layer encasing said core which comprises calcium silicate;
wherein said oleophillic active ingredient comprises greater than 50% by weight and less than 80% by weight of said particle. The particles of the invention preferably have a particle size in the range from about 100 µm to about 800 µm.

The coating can consist of calcium silicate alone or a mixture of calcium silicate with one of the following mixture components: microcrystalline cellulose, magnesium silicate, magnesium oxide, stearic acid, calcium stearate, magnesium stearate, silicon dioxide, kaolin and hydrogenated vegetable oil (e.g., STEROTEX, AC Humco, Memphis, Tenn.). Coatings which consist essentially of calcium silicate alone are preferred. In the case of a mixture of calcium silicate and a second coating material, the mixture is at least 50% by weight calcium silicate.

When the coating consists of calcium silicate alone, the amount of oleophilic substance can amount to above 70 wt. % without the aforementioned disadvantageous properties being present even to a small extent.

In the case of particles in accordance with the invention in which the coating consists of calcium silicate alone, the amount of calcium silicate lies in a range from 2 to 12 wt. %, preferably in the range from 5 to 9 wt. %. In this, in comparison to the state of the art, very low amount of coating substance lies the essential reason that a very high amount of active ingredient, namely a very high amount of oleophilic substance, can be incorporated in the matrix without the handling of the particles being influenced. The low amount of coating substance was surprising insofar as it is assumed that substances coming into consideration for this purpose and having a chemically inert behaviour would all adhere in about the same amounts to the carrier material of the matrix.

In the case of particles having a coating consisting of a mixture of calcium silicate with one or more of the aforementioned mixture components, the content of calcium silicate mixture lies between 5 and 25 wt. %.

It has, however, emerged that not only the chemical, but also the physical nature of the calcium silicate particles is of significance. Thus, it has surprisingly been found that calcium silicate particles are especially suitable when they have an average particle size of $\leq 0.2$ μm, especially $\leq 0.1$ μm, and a specific surface in a range from about 80 m$^2$/g to about 180 m$^2$/g, preferably in a range from about 95 m$^2$/g to 120 m$^2$/g, and are agglomerated to aggregates having an average size in a range from about 5 μm to about 20 μm, preferably in a range from about 5 μm to about 10 μm. The SiO$_2$/CaO ratio of the calcium silicate preferably lies between 1.65 and 2.65.

Further, it is advantageous when the calcium silicate is present wholly or partly in the form of the hydrate. The calcium silicate should also be practically free from crystalline silicic acid. Therefore, numerous calcium silicates available on the market as coating substances are excluded from use in the particles in accordance with the invention, since they have been treated with crystalline silicic acid.

Any oleophilic substance having pharmacological activity or micronutrient value may be used as the active substance in the particles of the invention. Preferably, the oleophilic substance is at least one from the following group: lipophilic vitamins, e.g., vitamins A, D, E, K and their derivatives, carotenoids, especially β-carotene, and polyunsaturated fatty acids such as, e.g., arachidonic acid, ecosapentaenoic acid and docosahexaenoic acid. The lipophilic vitamins are preferably vitamin A, vitamin A acetate, vitamin A palmitate, vitamin E or vitamin E acetate, especially vitamin E or vitamin E acetate.

Vitamin E includes synthetically manufactured tocopherols or natural tocopherols.

Any conventional carrier material for an oleophilic active substance may be used in accordance with the invention. The carrier material is preferably cellulose, water-soluble cellulose derivatives, especially methylcellulose or hydroxypropylmethylcellulose, maltodextrin, especially maltodextrin having a dextrose equivalent value of about 18, alginic acid derivatives, especially sodium, calcium or propylene glycol alginate, calcium lactate, gum arabic, gelatine, especially fish gelatine, sugar, sugar alcohol, glycerol, modified starch or pre-gelatinized cereal starch. The carrier is preferably gelatine, especially fish gelatine. Gelatine having a Bloom number between 0 and about 220 has proved to be especially good. The carrier material can additionally contain a water-soluble vitamin.

The flowable dry particles are well suited for the manufacture of solid dosage forms, especially tablets, since they have an outstanding flow and compressibility behaviour without the need for the addition of the usual amounts of compression aids.

Having regard to the possibility of incorporating an oleophilic active ingredient amount of 70 wt. % or above to nearly 80 wt. % (amounts of 74 wt. %, and, respectively, 78 wt. % have been incorporated without problems) in the particles in accordance with the invention, they are especially suitable for the manufacture of multivitamin and multimineral tablets, since in the case of these an amount of oleophilic active ingredient which is as high as possible coupled with a volume or weight which is as low as possible is sought after. Under the term "multivitamin and multimineral tablets" there are to be understood here also effervescent or chewable tablets.

Multivitamin tablets in accordance with the present invention are made using a composition of the invention which contains at least one oleophilic substance as an active ingredient from the group of carotenoids, especially, β-carotene, and vitamins A, D, E and K or a derivative thereof. When present, the vitamin E content in the multivitamin tablet is preferably between about 4 and 50 wt. %, especially about 5 and 19 wt. %. The multivitamin tablet preferably contains one or more water-soluble substances as an active ingredient, such as water soluble vitamins. In addition to the usual adjuvants, the dosage form may also contain trace elements, usually incorporated in the form of a mineral.

As trace elements there are used especially manganese, iodine, potassium, magnesium, calcium, phosphorus, zinc, copper and iron, with calcium being provided at least to some extent already by the coating of the particles in accordance with the invention. Of lesser importance there can also be used selenium, chromium, chlorine (as chloride), molybdenum, nickel, tin, silicon (bound), vanadium and boron, with silicon (bound) being incorporated at least in part, like calcium, by the particles in accordance with the invention. At least one substance from the group of vitamin C, $B_1$, $B_2$, $B_6$, $B_{12}$, pantothenic acid, calcium pantothenate, folic acid, biotin and nicotinamide is used as the water-soluble substance for the aforementioned purpose.

The composition of the invention may be manufactured by any conventional means by which particles of the admixed active ingredient and carrier are coated with sufficient calcium silicate to produce dry flowable particles. A preferred process for the manufacture of the dry flowable particles of the invention comprises spraying an aqueous emulsion of the oleophilic active substance and the carrier material into a catch medium according to a known powder catch process (e.g., the process of disclosed in U.S. Pat. No. 2,756,177, the disclosure of which is hereby incorporated by reference), where the catch medium is calcium silicate or of a mixture of calcium silicate with one or more mixture components as disclosed in more detail above, and subsequently drying the resulting particles in a manner known per se.

However, the most preferred process for producing the particles of the invention comprises spraying the aqueous emulsion of the oleophilic active substance and the carrier material in a spray tower into which the calcium silicate or the calcium silicate mixture disclosed herein is also sprayed so as to coat the aqueous emulsion. An example of such a process is U.S. Pat. No. 4,519,961, the disclosure of which is hereby incorporated by reference.

Further particulars and advantages will be evident from the following Examples.

Examples 1–3 describe particles which are coated only with calcium silicate.

Example 4 describes the coating with a mixture of calcium silicate and microcrystalline cellulose.

Examples 5–8 describe multivitamin tablets.

EXAMPLE 1

38 g of dried fish gelatine (Bloom number 0) were placed in a 500 ml vessel, 95 ml of de-ionized water were then added and the mixture was brought into solution while stirring with a mincer disc at 1000 revolutions/minute (rpm) at 40–50° C., which gave the matrix. Thereupon, 154 g of tocopherol acetate were emulsified in this matrix and stirred for 15 minutes. During the emulsification and stirring the mincer disc was rotated at 4800 rpm. After this time the internal phase of the emulsion had an average particle size of about 250 nm. The emulsion was then diluted with 130 ml of deionized water and heated to 65° C. Subsequently 225 g of calcium silicate (Micro-Cel E from Celite Corp., USA with a SiO$_2$/CaO ratio of 1.65) were placed in a laboratory spray tank cooled below 0° C. with dry ice. The emulsion was sprayed into the spray tank using a rotating spray nozzle. The thus-obtained particles coated with calcium silicate were sieved off (sieve fraction 100–800 μm) from the excess calcium silicate and dried at room temperature using a stream of air. There were obtained 190 g of particles coated with calcium silicate which had outstanding flow properties, were completely dry and could be handled very well. The tocopherol acetate content of the particles was 72.0% and the calcium silicate content was 7 wt. %.

EXAMPLE 2

In an experiment analogous to Example 1, the fish gelatine was replaced with a gelatine for pharmaceutical purposes having a Bloom number of 220 from Croda, England. The yield was 195 g. The product contained 76.1 wt. % tocopherol acetate, 6.2 wt. % calcium silicate, and had the same good industrially applicable properties as that of Example 1.

EXAMPLE 3

Example 1 was repeated analogously, but using a calcium silicate having a $SiO_2/CaO$ ratio above 2.65 ($SiO_2/CaO$ ratio=3.9). Particles coated with calcium silicate formed, and had a tocopherol acetate content of only 44.3 wt. %. The weight content of calcium silicate rose to above 7 wt. %. A calcium silicate having a $SiO_2/CaO$ ratio of above 2.65 is therefore unsuitable.

EXAMPLE 4

36 g of high molecular weight, dried fish gelatine (Bloom number 0; Norland Products Incorporated) were placed in a 500 ml vessel. 95 ml of deionized water were then added and the mixture was brought into solution while stirring with a mincer disc at 1000 revolutions/minute (rpm) at 40–50° C., which gave the matrix. Thereupon, 156 g of tocopherol acetate were emulsified in the matrix and stirred for 15 minutes. During the emulsification and stirring the mincer disc was rotated at 4800 rpm. After this time the internal phase of the emulsion had an average particle size of about 300 nm. The emulsion was then diluted with 135 ml of deionized water and heated to 65° C. Subsequently, 410 g of a mixture of calcium silicate (Micro-Cel E from Celite Corp., USA with a $SiO_2/CaO$ ratio of 1.65) and microcrystalline cellulose (VTVAPUR Type 105) were placed in a laboratory spray tank. The ratio of VIVAPUR Type 105 to Micro-Cel E was 5.66:1. The coating mixture was cooled to below 0° C. with dry ice. The emulsion was sprayed into the spray tank using a rotating spray nozzle. The thus-obtained particles coated with calcium silicate-cellulose were sieved off (sieve fraction 100–800 μm) from excess calcium silicate-cellulose mixture and dried at room temperature using a stream of air. There were obtained 222.1 g of particles coated with calcium silicate-cellulose which had outstanding flow properties, were completely dry and could be handled very well. The tocopherol acetate content was 64.2 wt. %, and the total coating content was 21 wt. %.

EXAMPLE 5

Multivitamin tablets were manufactured from the following components on a Comprex II tabletting machine, punch 16×7.42 mm, under pressures of 5 to 50 KN.

| | |
|---|---|
| Particles from Example 1 | 147.0 mg |
| 7.5% β-carotene* | 96.0 mg |
| Ascorbic acid 90% gr. | 244.5 mg |
| Microcrystalline cellulose** | 130.0 mg |
| Lactose*** | 50.0 mg |
| Total tablet weight | 668.0 mg |

*Beta-Tab 7.5, F. Hoffmann-La Roche Ltd, Basel, Switzerland
**Avicel PH 102, FMC Corp., Phila. Pa.
***Pharmatose DCL 2 1, DMV Campina Inc., La Crosse, Wi.

The resulting tablet hardness was 20 to 140 N. The tablets were dry.

EXAMPLE 6

Analogously to Example 4, a multivitamin tablet (E 75% formula, containing 75 wt. % vitamin E particles) was manufactured using particles in accordance with the invention having a vitamin E content of 75 wt. % as the active ingredient and compared with a conventional vitamin tablet (E 50% formula, containing 50 wt. % vitamin E particles) of the same composition.

| | E 75% formula | E 50% formula |
|---|---|---|
| Tablet weight | 808.3 mg | 948.3 mg |
| 20% β-Carotene* | 34.5 mg | 34.5 mg |
| Vitamin E | 280.0 mg | 420.0 mg |
| Vitamin C 90 | 291.7 mg | 291.7 mg |
| Microcrystalline cellulose** | 161.6 mg | 161.6 mg |
| Calcium silicate*** | 24.3 mg | 24.3 mg |
| Polyvinyl pyrrolidone**** | 16.2 mg | 16.2 mg |

*Beta-Tab 20, F. Hoffmann-La Roche Ltd, Basel, Switzerland
**Avicel PH 102, FMC Corp., Phila., Pa.
***Microcel C, Celite Corp., Lompoc, Ca.
****Polyplasadone XL, ISP, Wayne, N.J.

From this it will be evident that, with the particles in accordance with the invention, there can be manufactured tablets having a lower weight (or correspondingly lower volumes) than with conventionally manufactured particles containing vitamin E.

EXAMPLE 7

Analogously to Example 5, a multivitamin tablet (E 75% formula, containing 75 wt. % vitamin E particles) was manufactured using particles in accordance with the invention having a vitamin E content of 75 wt. % as the active ingredient and compared with a conventional vitamin E tablet (E 50% formula, containing 50 wt. % vitamin E particles) of the same composition.

| | E 75% formula | E 50% formula |
|---|---|---|
| Vitamin/mineral mixture | 1294.8 mg | 1294.8 mg |
| Vitamin E | 70.7 mg | 106.0 mg |
| Microcrystalline cellulose* | 57.2 mg | 0.0 mg |
| Polyvinyl pyrrolidone** | 6.6 mg | 30.0 mg |
| Stearic acid | 2.0 mg | 2.0 mg |
| Magnesium stearate | 4.2 mg | 4.2 mg |

*Avicel PH 102, FMC Corp., Phila., Pa.
**Polyplasadone XL, ISP, Wayne, N.J.

The resulting tablet hardness was 210N. In the case of E 75% formula the amount of disintegrant PVP XL could be reduced without changing the dissolution time of the tablet (less than 5 minutes).

EXAMPLE 8

Analogously to Example 5, a multivitamin tablet (E 75% formula, containing 75 wt. % vitamin E particles) was manufactured using particles in accordance with the invention having a vitamin E content of 75 wt. % as the active ingredient. The tablets contained no disintegrant and had the following composition.

|  | E 75% formula |
| --- | --- |
| Vitamin/mineral mixture | 1294.8 mg |
| Vitamin E | 70.7 mg |
| Microcrystalline cellulose* | 58.0 mg |
| Starch | 15.0 mg |
| Stearic acid | 2.0 mg |
| Magnesium stearate | 4.2 mg |

*Avicel PH 102, FMC Corp., Phila., Pa.

The resulting tablet hardness was 210N. The dissolution time of the tablet was less than 5 minutes.

We claim:

1. A flowable dry particle having a size in the range from about 80 μm to about 1000 μm comprising:
   a core comprising an oleophilic active ingredient dispersed in a carrier material, and
   a coating layer encasing said core which comprises calcium silicate;
   wherein said oleophillic active ingredient comprises greater than 50% by weight and less than 80% by weight of said particle.

2. The particle of claim 1 wherein the coating layer consists essentially of calcium silicate which is present in an amount in the range from 2% by weight to 12% by weight of said particle.

3. The particle of claim 2 wherein the oleophilic active ingredient is a lipophilic vitamin, a carotenoid, or a polyunsaturated fatty acid, and the carrier material comprises cellulose, water-soluble cellulose derivatives, maltodextrin, an alginic acid derivative, calcium lactate, gum arabic, gelatine, sugar, sugar alcohol, glycerol, modified starch and pregelatinized cereal starch.

4. The particle of claim 3 wherein the calcium silicate has an average particle size of ≦0.2 μm, a specific surface in the range from about 80 m$^2$/g to about 180 m$^2$/g, is agglomerated in aggregates having an average size in the range from about 5 μm to about 20 μm and has an SiO$_2$/CaO ratio in the range from 1.65 to 2.65.

5. The particle of claim 4 wherein the calcium silicate is present in an amount in the range from about 5% by weight to about 9% by weight of said particle, and the oleophillic active ingredient is present in an amount which is greater than 70% by weight and less than 80% by weight of said particle.

6. The particle of claim 5 having a size in the range from about 100 μm to about 800 μm wherein the carrier material consists essentially of gelatine.

7. The particle of claim 6 wherein the oleophilic active ingredient is a lipophilic vitamin.

8. The particle of claim 7 wherein the oleophilic active ingredient is vitamin A, vitamin E or a vitamin A or vitamin E derivative.

9. The particle of claim 8 wherein the oleophilic active ingredient is vitamin A, vitamin A acetate, vitamin A palmitate, vitamin E or vitamin E acetate.

10. The particle of claim 9 wherein the oleophilic active ingredient is vitamin E acetate.

11. The particle of claim 10 wherein the core further comprises a water soluble vitamin.

12. The particle of claim 1 wherein the coating layer consists essentially of calcium silicate and a second coating material admixed therewith selected from the group consisting of microcrystalline cellulose, magnesium silicate, magnesium oxide, stearic acid, calcium stearate, magnesium stearate, silicon dioxide, kaolin and hydrogenated vegetable oil, wherein the calcium silicate comprises at least 50% by weight of the coating layer, and the coating layer is present in an amount in the range from 5% by weight to 25% by weight of said particle.

13. The particle of claim 12 wherein the oleophilic active ingredient is a lipophilic vitamin, a carotenoid, or a polyunsaturated fatty acid, and the carrier material comprises cellulose, water-soluble cellulose derivatives, maltodextrin, an alginic acid derivative, calcium lactate, gum arabic, gelatine, sugar, sugar alcohol, glycerol, modified starch and pregelatinized cereal starch.

14. The particle of claim 13 wherein the calcium silicate has an average particle size of ≦0.2 μm, a specific surface in the range from about 80 m$^2$/g to about 180 m$^2$/g, is agglomerated in aggregates having an average size in the range from about 5 μm to about 20 μm, and has an SiO$_2$/CaO ratio in the range from 1.65 to 2.65.

15. The particle of claim 14 wherein the calcium silicate is present in an amount in the range from about 5% by weight to about 9% by weight of said particle, and the oleophillic active ingredient is present in an amount which is greater than 70% by weight and less than 80% by weight of said particle.

16. The particle of claim 15 having a size in the range from about 100 μm to about 800 μm wherein the carrier material consists essentially of gelatine.

17. The particle of claim 16 wherein the oleophilic active ingredient is a lipophilic vitamin.

18. The particle of claim 17 wherein the oleophilic active ingredient is vitamin A, vitamin E or a vitamin A or vitamin E derivative.

19. The particle of claim 18 wherein the oleophilic active ingredient is vitamin A, vitamin A acetate, vitamin A palmitate, vitamin E or vitamin E acetate.

20. The particle of claim 19 wherein the oleophilic active ingredient is vitamin E acetate.

21. The particle of claim 20 wherein the core further comprises a water soluble vitamin.

* * * * *